United States Patent
Karthe et al.

(10) Patent No.: US 6,534,011 B1
(45) Date of Patent: Mar. 18, 2003

(54) DEVICE FOR DETECTING BIOCHEMICAL OR CHEMICAL SUBSTANCES BY FLUORESCENCE EXCITATION

(75) Inventors: Wolfgang Karthe, Jena (DE); Andreas Bräuer, Schlöben (DE); Frank Eismann, Jena (DE); Michael Köhler, Golmsdorf (DE); Ralf Waldhäusl, Jena (DE); Norbert Danz, Jena (DE)

(73) Assignees: Fraunhofer-Gesellschaft zur Forderung der angewandten Forschung e.V., Munich (DE); Institut fur Physikalische Hochtechnologie, Jena (DE)

( * ) Notice: Subject to any disclaimer, the term of this patent is extended or adjusted under 35 U.S.C. 154(b) by 0 days.

(21) Appl. No.: 09/445,819
(22) PCT Filed: Jun. 11, 1998
(86) PCT No.: PCT/EP98/03535
§ 371 (c)(1), (2), (4) Date: Jan. 7, 2000
(87) PCT Pub. No.: WO98/57151
PCT Pub. Date: Dec. 17, 1998

(30) Foreign Application Priority Data

Jun. 13, 1997 (DE) .......................... 197 25 050

(51) Int. Cl.⁷ .............................................. G01N 21/64
(52) U.S. Cl. .................... 422/82.01; 422/82.11
(58) Field of Search .......................... 422/82.05, 82.07, 422/82.08, 82.11; 436/172; 250/458.1, 459.1; 385/12

(56) References Cited

U.S. PATENT DOCUMENTS

| | | | | |
|---|---|---|---|---|
| 5,677,196 A | * | 10/1997 | Herron et al. | 436/518 |
| 5,779,978 A | * | 7/1998 | Hartmann et al. | 422/82.05 |
| 5,827,748 A | * | 10/1998 | Golden | 436/527 |
| 5,854,684 A | * | 12/1998 | Stabile et al. | 356/440 |

FOREIGN PATENT DOCUMENTS

| | | |
|---|---|---|
| EP | 0194132 | 9/1986 |
| EP | 0519622 | 12/1992 |
| EP | 0723146 | 7/1996 |
| WO | WO 92/21020 | 11/1992 |
| WO | WO 95/03538 | 2/1995 |

\* cited by examiner

Primary Examiner—Jeffrey Snay
(74) Attorney, Agent, or Firm—Leydig Voit & Mayer, Ltd.

(57) ABSTRACT

The invention relates to an arrangement for the detection of biochemical or chemical substances using fluorescent light excitation, and to a process for its production, which can be used in a variety of fields, for example in biotechnology, in molecular medicine, in pharmaceuticals development and for the analysis or various chemical substances. A relatively simple structure is intended to provide the invention with the possibility of being able to carry out the detection of a large number of samples in a very short time with a high degree of accuracy. To that end, a laminar substrate is formed with a locally defined structure in order to detect different samples. Advantageously, on the detector side, a lens array designed according to the structuring can be used to project the fluorescent light from the different samples on to a detector array. It is, however, also possible to place a detector array matched to the structuring of the substrate on the substrate, or arrange it there.

22 Claims, 5 Drawing Sheets

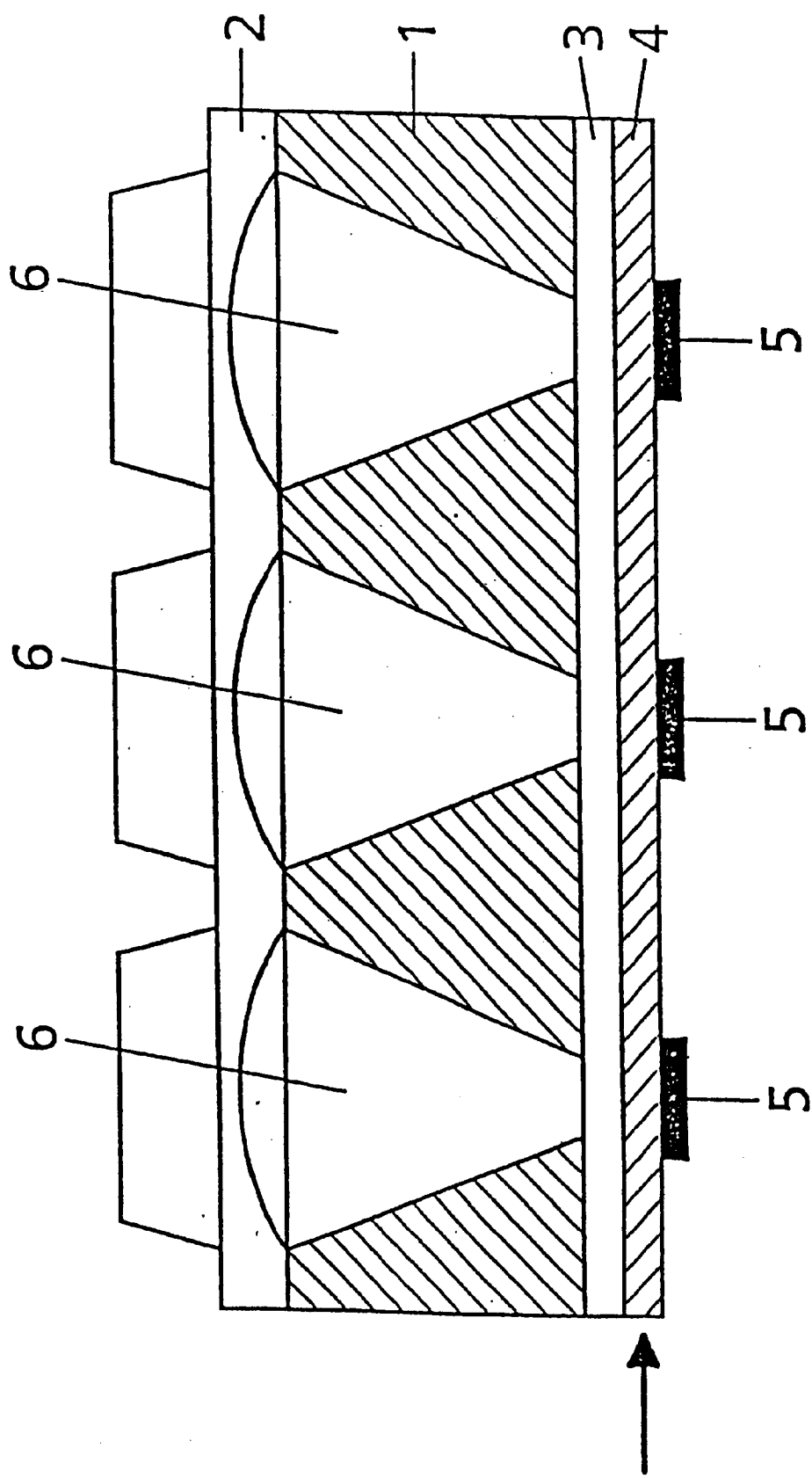
Figur 1

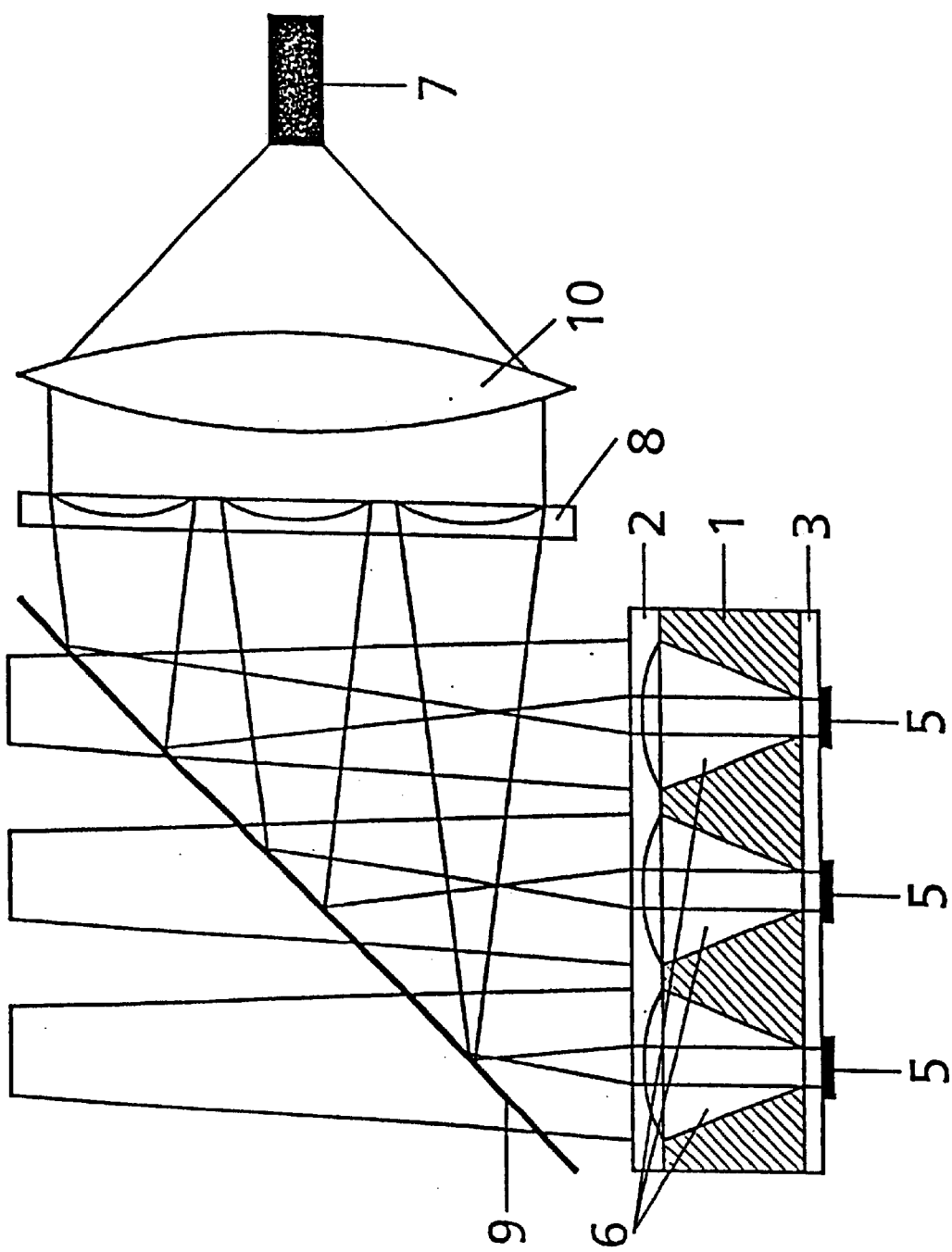
Figur 2

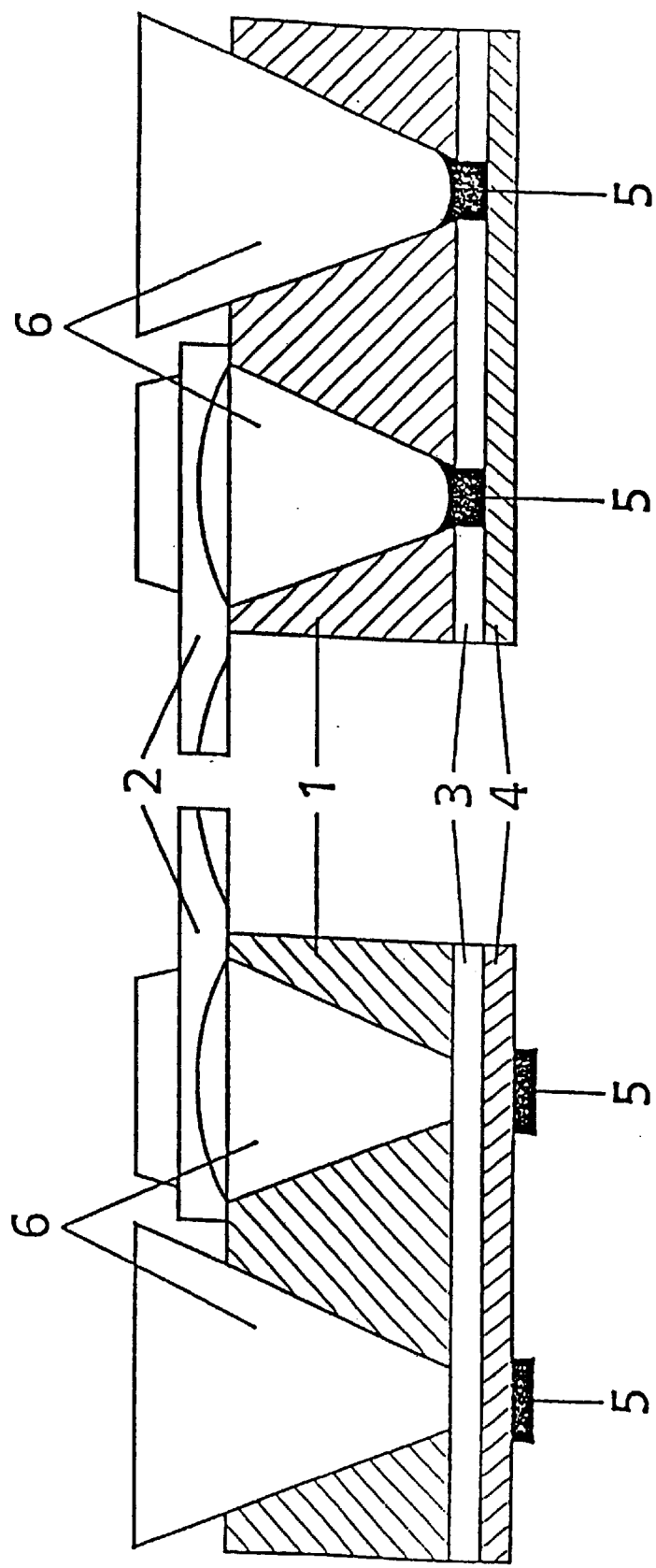
Figur 3a
Figur 3b

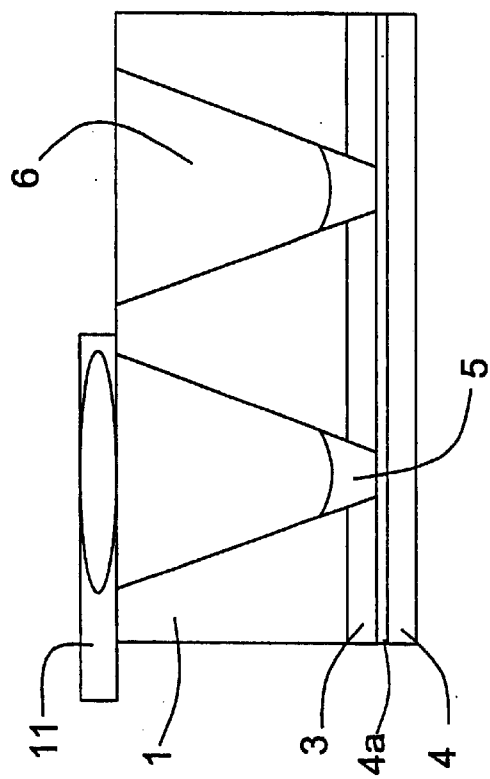
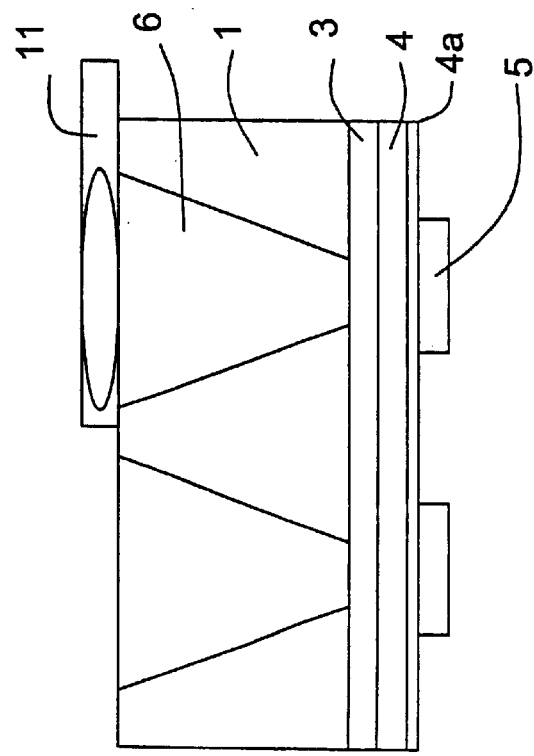

DEVICE FOR DETECTING BIOCHEMICAL OR CHEMICAL SUBSTANCES BY FLUORESCENCE EXCITATION

The invention relates to an arrangement for the detection of biochemical or chemical substances using fluorescent light excitation, and to a process for the production of such an arrangement. The arrangement according to the invention can be used in a variety of fields, for example in biotechnology, in molecular medicine, in pharmaceuticals development and for the analysis of various chemical substances.

For a considerable time, a wide variety of optical methods and systems have been used, for example for research into various biological systems and processes, in microbiology and molecular medicine. In this case, spectrometers are often used, which permit a relatively high information content with correspondingly high accuracy when they are employed. Spectrometers are, however, unsuitable for many routine experiments that are encountered, since elaborate preparation of the individual samples is required, and the time needed for the measurements is too long and can lead to denaturing of the samples.

For many applications, solutions are required with which rapid, accurate and inexpensive analysis of a very large number of samples (of the order of $10^6$) can be carried out. Examples of such applications include DNA libraries.

A variety of measurement techniques have to date been used for analysis and detection. For example, variation in absorption, variation in refractive index or the fluorescent light excited are determined. In the case of measuring the intensity of fluorescent light, the excitation light and the modified fluorescent light can be directed parallel or perpendicular to one another.

If the two different types of light are directed perpendicular to one another, the formation of an evanescent field along a waveguide is utilized. This form is used, for example, to detect antigen-antibody reactions. In these so-called "solid-phase fluoroimmunoassays", the detection-specific antibodies are immobilized on a sensor surface. The analyte (antigen) is bound to a corresponding antibody and can then be detected by being made to fluoresce by the evanescent field either directly or with the use of a marker. Excitation of fluorescence by the evanescent field of a waveguide gives the advantage that the penetration depth of the evanescent field is limited (about 100 to 200 nm) and only analytes or markers bound directly to the sensor surface are therefore excited. The result of this is that the measurable intensity of the fluorescent light is a direct measure of the number or concentration of bound analyte or marker, and for this reason it is possible to do without additional washes to remove unbound marker molecules.

Both optical fibres and layer waveguides can be used for such optical waveguides. Optical fibres have the advantage that corresponding sensors or devices are simple and inexpensive to produce. They can be used in virtually any places, even ones which are very inaccessible, and the measurement signals can be transmitted optically with ease over considerable distances. For example, U.S. Pat. Nos. 4,447,546 and 4,909,990 disclose that, although optical fibres can in principle be used for corresponding processes, flat layer waveguides are generally used.

Flat layer waveguides have the advantage that a very wide variety of substances that been to be analysed, and immobilizing layers which may be necessary, can be applied and structured with ease. Examples of methods which can be used for this include spin-on coating, pouring, sputtering and known vacuum evaporation methods. Furthermore, a plurality of individual sensors can be produced on a single large plate, with the sensors produced in this way having virtually the same properties. Another advantage of such sensor structures is that they are very stable, and consequently are also very easy to handle. A very wide variety of layer materials can be applied and structured with ease. In this case, a very wide variety of metals, glasses and polymers can be used.

It is readily possible for flat laminar structures to be used in detection instruments, and for optical measurement methods to be carried out in them.

The production and structuring of flat structures of this type has been tried and tested from previous experience in microelectronics fabrication, and the associated costs are therefore relatively low.

Biological sensor structures which use the formation of evanescent fields for fluorescent light excitation are, for example, [lacuna] by S. Sjölander and C. Urbaniczky: Integrated Fluid Handling System for Biomolecular Analysis, Anal. Chem., 63 81991) 2338–2345 and R. Cush et al.: The resonant mirror: a novel optic biosensor for direct sensing of biomolecular interactions. Part 1: principles of operation and associated instrumentation. Biosensors Bioelectron., 8 (1993) 347–353 and J. E. Fletcher et al.: A Rapid, Biosensor-based, assay for PSA in Whole Blood, Tumor Marker Update Vol. 5, No. 5 (1993). The detection limits for the sensor described by S. Sjölander and C. Urbaniczky are thus 0.5 ng/ml (FCFD).

Another device for fluorescent detection of biological reactions using evanescent field excitation of a layer waveguide is described in WO 94/27137, in which case there is a detection limit when using a reference channel at $10^{-13}$ molar solutions.

In this solution, use is made of a planar waveguide on whose surface separate fields are provided, on or in which trapping molecules are immobilized and it is also possible for different samples to be determined using evanescent field excitation in the form of fluorescence immunoassays for the different fields. In this case, the light is necessarily injected into the planar waveguide through an end face of the planar waveguide, and in a preferred embodiment through a lens-like configuration of this end face, and the evanescent field is formed and the fluorescence excited at the interface. The fluorescent light emerges at the opposite side of the waveguide and can be measured using the usual detectors, it being possible to control the optical path using various optical elements. This gives rise to two significant disadvantages, which, as mentioned above, have a negative effect on the measuring sensitivity. On the one hand, it is not possible to prevent the different samples that the fields contain from affecting the fluorescent light, since complete optical isolation is impossible, and on the other hand problems arise owing to the injection of the light exclusively through the end of the waveguide, so that it is necessary to put up with relatively large losses of light.

Although, in this case, the use of appropriate optical filters has been proposed to reduce the effect of stray light, these also cause loss of fluorescent light and the aforementioned effect of the present light from the various samples cannot be prevented entirely.

EP 0 519 622 A2 describes another device for carrying out assays using evanescent field excitation, in which tapering openings in a silicon substrate and the containment thus obtained is filled with a liquid by which an ion-selective membrane is formed.

The solutions described by S. Sjölander and C. Urbaniczky, and R. Cush et al., detect changes in refractive index that are caused by the build-up of analytes on the surface. The measured change in refractive index does not, however, involve only the particular build-up to be investigated, and the selectivity that can be obtained is consequently not always what it could be. For the measurements carried out in that way, very high outlay on equipment is necessary, which is also reflected in relatively high costs. It is not possible to examine a plurality of samples at the same time.

In the biosensor described by J. E. Fletcher et al., the relatively extensive excitation of fluorescence, and its evanescent injection into a layer waveguide in FCFD, leads to relatively low sensitivity.

EP 0 723 146 A1 and EP 0 194 132 A2 describe other possible ways of detecting biochemical or chemical substances using fluorescent light excitation, both cases describing the arrangement of different samples in a predetermined system and their evaluation. EP 0 723 146 A1 describes examples in which various samples are immobilized next to one another, and CCDs or individual lenses in an arrangement designed according to the sample arrangement are used for the evaluation.

The object of the invention is to provide a way in which it is possible to detect a relatively large number of samples relatively simply and with high accuracy in a very short time.

This object preferably is achieved by the characterizing features of the present invention. Advantageous embodiments and further developments of the solution will be apparent from the description of the invention provided herein.

The arrangement according to the invention consists essentially however, it is also possible to use a lens matched to the structuring, for example a Fresnel lens, for this. A buffer layer, and a waveguide array formed corresponding to the structuring made in the substrate, can be applied on the other side of the substrate from the lens array.

Each of the microstructures made in the substrate defines a fluorescence excitation and detection channel respectively for one of the samples to be detected.

There are principle two ways of exciting the fluorescent light. First, the evanescent field may be formed in a waveguide array that is formed on the side of the substrate opposite the detector side. The second possible excitation method is to direct the excitation light on to the individual samples through the lens array matched to the structuring in the substrate, it being in each case possible for the fluorescent light to be focused on to the detector using the lens array arranged on the detector side of the substrate. For this purpose, the detector is likewise designed in the form of an array, for example as a CCD array, so that the fluorescent light from each individual sample can be detected separately.

For the case of evanescent field excitation, however, another possibility is to do without a lens array and, instead, to fit a detector array matched to the structuring on the substrate, or arrange the latter in such a way that the various samples can be detected selectively.

The structuring of the substrates, which may for example have the 4"×4" format known from a semiconductor technology, is easy and inexpensive to produce using the silicon processing methods known from this field, and in this case, microstructuring can be achieved on such a substrate which allows a sample number of up to $10^6/cm^2$.

The substrate to be used according to the invention can advantageously ensure that a very wide variety of fluorescent signals, which are to be evaluated using the detector array, do not affect one another or become superimposed, so that each sample can be uniquely assigned a measurement without interference. To that end, the substrate preferably consists of a material which absorbs the fluorescent light at its wavelengthis). Another way of achieving the same effect is, however, to design the respective walls in the structuring of the substrate such that they reflect, so that this undesirable effect can be avoided.

The preferred structuring in the substrate, by forming pyramid or conical, or upright openings, has the further advantage that the fluorescent light is favourably reflected and therefore concentrated in the direction of the lens array, and consequently can also be directed at the respective detectors.

With the arrangement according to the invention, it is possible to detect molecule concentrations equal to $10^{-12}$ molar or less, in a large number of different samples in a very short time. Further, the exciting light can be directed at the respective sample in an exactly defined way, and the respectively corresponding fluorescent light can be directed, while substantially avoiding contributions from the stray light or other interference, directly at the respective detector assigned to an individual sample, and the corresponding analyte may where appropriate also be determined quantitatively.

With the solution according to the invention, not only can improved spatially resolved measurement be carried out, but there is also optionally the possibility of taking time-resolved measurements using a corresponding time-controllable detector arrangement (e.g. triggerable CCD camera and electronic delay unit).

The invention will be explained in more detail below with reference to illustrative embodiments.

In the figures:

FIG. 1 shows an illustrative embodiment of an arrangement according to the invention with fluorescence excitation using an evanescent field;

FIG. 2 shows a second illustrative embodiment of an arrangement according to the invention with fluorescence excitation using a microlens array;

FIG. 3a shows an arrangement according to FIG. 1 with and without a lens array; sample on the restructured side;

FIG. 3b shows an arrangement having openings extending as far as the waveguide layer, with and without a lens array, and samples in openings;

FIG. 4a shows an arrangement with an additional interlayer and samples arranged under the waveguide and substrate;

FIG. 4b shows an arrangement with an additional interlayer and samples arranged above the waveguide(s)

Figure 5:
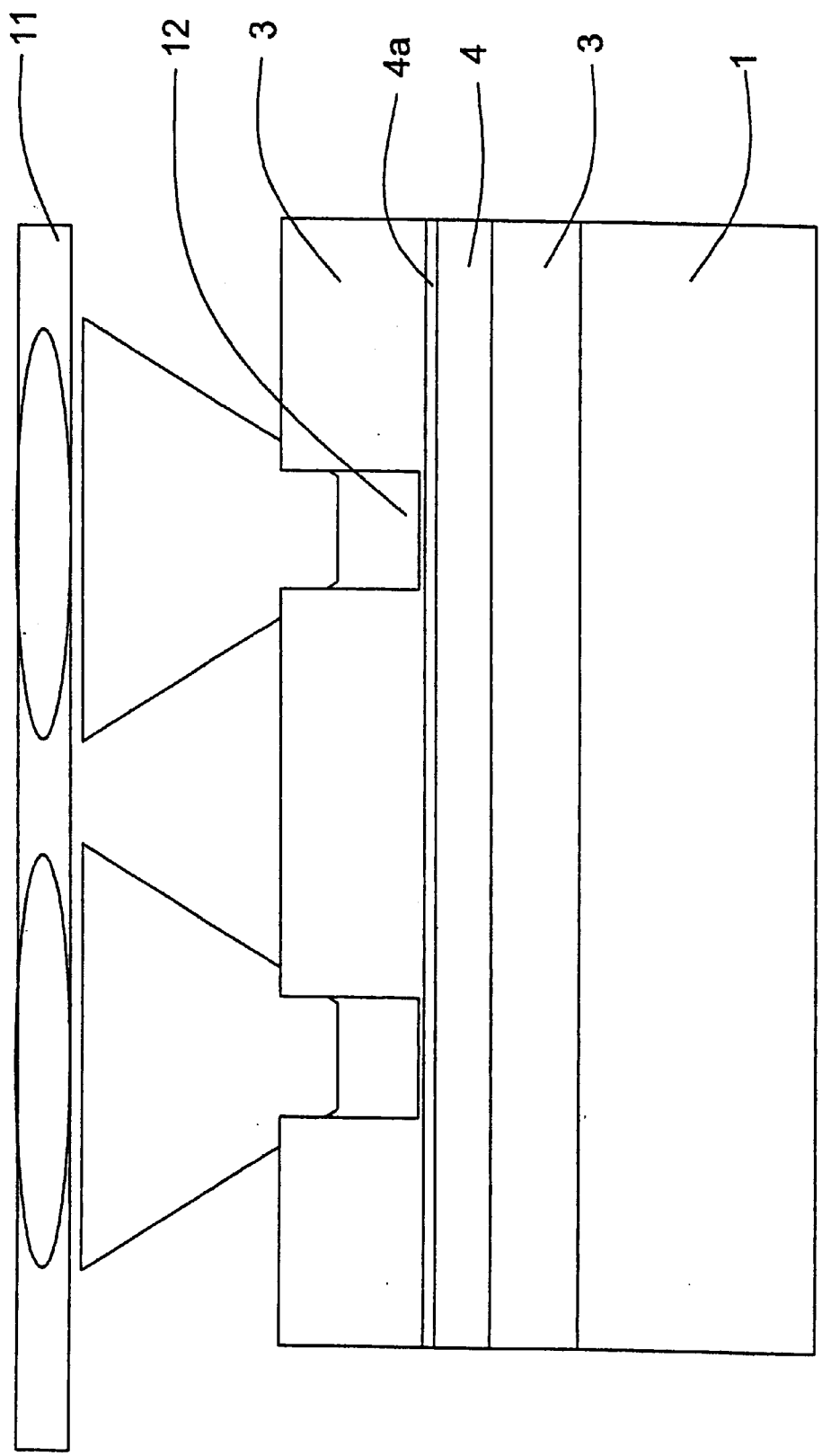
FIG. 5 shows an arrangement with a structured buffer layer.

In the example of an arrangement according to the invention which is represented in FIG. 1, use is made of a silicon substrate 1, e.g. a known silicon wafer, which is provided on one side with a layer sequence of doped silicon dioxide or another silicate. In this case, the layer sequence consists of a buffer layer 3 and a waveguide layer 4.

On the opposite side, that is to say the side facing a detector array (not shown), openings 6 are created in the substrate 1 in the form of a regular array. The openings 6 can, for example, be made in the silicon substrate 1 by anisotropic etching, in which case the silicon dioxide acts as an etch layer and the openings 6 consequently end at the silicon dioxide layer, i.e. at the buffer layer 3.

The openings 6 may in this case have pyramidal and conical shape, or cuboid shape, and are used to separate the various fluorescent light beams for the respective samples 5 which are assigned under the waveguide layer 4 to the openings 6, and are preferably applied using respective selective immobilizing layers. The samples 5 may in this case have both liquid and solid consistency, depending on the case.

If the fluorescence is being excited using the evanescent field of the waveguides 4, the fluorescent light for each sample 5 is directed at a detector of the detector array through the corresponding opening 6 via one of the lenses of the lens array 2, in which case one individual detector of the detector array is in each case assigned to one sample 5, and the fluorescence intensity can consequently be measured for each respective sample 5.

Besides silicon, it is also possible to use other substrate materials, for example various polymers which, for example, may be coloured, and the fluorescent light from various samples is thus absorbed so that crosstalk between the detection channels can be avoided. In the case, for example of polymer substrate materials, besides etching methods (dry etching methods), they may also be structured using appropriate laser processing or using replication techniques.

In the example of an arrangement according to the invention represented in FIG. 2, a substrate 1 is once more provided with a buffer layer 3 on which various samples 5 assigned to the respective openings 6 can be immobilized. Fitted inside the substrate 1, that is to say again in the direction towards the detector (not shown), a lens array 2 is placed which has individual lenses assigned to one opening 6, with the aid of which the fluorescent light can be directed at a respective detector of the detector array.

The fluorescence is excited by using at least one light source 7, which may preferably be a laser or a laser diode.

If the fluorescence is being excited using a microlens array, the light from the light source 7 passes through an objective 10 on to a second lens array 8 and is directed there by a semisilvered mirror 9, through a respective opening 6, on to the individual sample 5. The fluorescent light from the respective sample 5 cannot pass through the semisilvered mirror 9 in the direction of the detector array (not shown). The number of individual lenses in the two lens arrays 2 and 8 is identical, the arrangement of the individual lenses in the lens array 8 being chosen precisely in such a way that, in each case, light can be detected through a lens of the second lens array 8 via the semisilvered mirror 9 precisely through an opening 6 towards a sample 5 to excite the fluorescent light.

If required, however, it is also possible to use two light sources, which emit light at different wavelengths, or in different wavelength spectra, in which case it is more favourable to use separate respective second waveguide arrays 8 for this purpose.

It is, however, also possible to use filters and/or polarizers before and after the individual lenses of the lens arrays 2 and 8, in order to reduce the effect of error further.

In an additional operation, which is independent of the production of the openings 6, the arrangement shown in FIGS. 1 and 3a with the waveguide layer 4 is treated using a coating, masking and structuring process, so as to produce a strip waveguide array whose structure is matched to the structure with the opening 6 which is formed in the substrate 1.

Subsequent to this, different selective immobilization layers, assigned to the various openings 6, may then be applied so that different analytes can be immobilized and detected in each case.

Such a modified sensor surface may advantageously form the outlet of a continuous-flow measurement cell through which the sample and reference solutions can be introduced.

FIG. 3b shows another example of an arrangement according to the invention. In this example, the silicon dioxide buffer layer 3 has also been etched through, and cavities have been created to hold samples. In this case, the waveguide layer 4 at the bottom of the respective openings 6 is provided with an immobilizing layer for the different substances (biomolecules). The respective samples can be introduced into the openings 6, for example using a known pipetting device, and the fluorescence can be excited as in the description of FIG. 2.

FIGS. 4a and 4b show possible variants for the arrangement of an additional interlayer 4a which is intended to improve the immobilizing of the samples. Such an interlayer 4a is made of a material transparent to the excitation light and is formed with a small thickness (about 10 to 50 nm), which ensures that the formation of the evanescent field is affected only very slightly or not at all.

Examples of suitable materials include silicate and quartz, which can be applied using the same method as the one used to form the waveguides. It is, however, also possible to use optically and biologically or chemically suitable polymers as the interlayer material.

In the example according to FIG. 4b, such an interlayer 4a may also (the way in which this can be done is not shown) be formed as a thin film of liquid in the openings 6 in the substrate 1 immediately between the buffer layer 3 and the sample 5.

In the representation according to FIG. 4a, the samples 5 are arranged under the waveguides 4, the additional interlayer 4a being formed between the samples 5 and the waveguides 4. On top, there is again a buffer layer 3 and a structured substrate 1. In this example, a microobjective 11 is optionally arranged over the structured substrate 1 in front of the detector (not represented).

In the example shown in FIG. 4b, the samples 5 are held in the openings 6 of the substrate 1, and the interlayer 4a is arranged between the samples 5 and the buffer layer 3.

The example represented in FIG. 5 uses a structured buffer layer 3a, in which openings 12 are formed. The samples 5 can once more be immobilized on the additional interlayer 4a in these openings 12. The remainder of the corresponding arrangement is here again formed from the following individual elements: substrate 1 (which it is optionally possible to omit), waveguides 4 and buffer layer 3, it being in this case possible for the substrate to be unstructured.

The buffer layer 3a provided with the openings 12 is made of a material which affects the wave-guiding, if at all, only slightly. The openings 12 are designed and dimensioned in such a way that the evanescent field of the waveguides 4 does not, in the gaps between the openings 12, reach the surface of the buffer layer 3, and interference with the fluorescent light is prevented. The fluorescence can be excited as described above, and the fluorescent light emerges from the openings 12 through a corresponding aperture and can be directed using the microobjective 11 shown here, or a lens array 2 or a structured lens, at a detector array (not shown) for spatially resolved evaluation of the individual fluorescence intensities.

What is claimed is:

1. An arrangement for the detection of biochemical or chemical substances using fluorescence excitation, comprising:

a buffer layer comprising a top surface and a bottom surface;

a laminar substrate comprising a top surface and a bottom surface, the bottom surface of the laminar substrate contacting the top surface of the buffer layer, the laminar substrate defining a plurality of fluorescence channel openings therein; and a waveguide layer comprising a top surface and a bottom surface, the top surface of the waveguide layer contacting the bottom surface of the buffer layer.

2. The arrangement according to claim 1, wherein the fluorescence channel openings are formed as pyramids or cones or in upright form in the laminar substrate and extend at least as far as the buffer layer.

3. The arrangement according to claim 1, further comprising a plurality of lenses arranged on the top surface of the laminar substrate, each lens arranged in conjunction with a fluorescence channel opening.

4. The arrangement according to claim 1, further comprising a lens contacting the top surface of the laminar substrate.

5. The arrangement according to claim 1, further comprising a plurality of detectors arranged on the top surface of the laminar substrate, each detector arranged in conjunction with a fluorescence channel opening.

6. The arrangement according to claim 1, wherein the laminar substrate consists of a material that absorbs fluorescent light or is designed so as to reflect or absorb fluorescent light.

7. The arrangement according to claim 1, wherein the fluorescence channel openings are defined by at least one wall that reflects fluorescent light.

8. The arrangement according to claim 1, wherein the laminar substrate consists of silicon, glass, vitreous material, or a polymer and the buffer layer and waveguide layer consist of a silicate, glass, vitreous material, or a polymer.

9. The arrangement according to claim 1, further comprising a plurality of sample immobilization areas arranged on the bottom surface of the waveguide layer, each sample immobilization area arranged in conjunction with a fluorescence channel opening.

10. The arrangement according to claim 9, further comprising a plurality of immobilization layers contacting a plurality of the sample immobilization areas.

11. The arrangement according to claim 1, further comprising:

an interlayer transparent to fluorescence excitation, the interlayer comprising a top surface and a bottom surface, the top surface of the interlayer contacting the bottom surface of the waveguide layer; and a plurality of sample immobilization areas arranged on the bottom surface of the interlayer, each sample immobilization area arranged in conjunction with a fluorescence channel opening.

12. The arrangement according to claim 11, further comprising a plurality of immobilization layers contacting a plurality of the sample immobilization areas.

13. An arrangement for the detection of biochemical or chemical substances using fluorescence excitation, comprising:

a buffer layer comprising a top surface and a bottom surface;

a laminar substrate comprising a top surface and a bottom surface, the bottom surface of the laminar substrate contacting the top surface of the buffer layer, the laminar substrate defining a plurality of fluorescence channel openings therein;

an interlayer transparent to fluorescence excitation, the interlayer comprising a top surface and a bottom surface, the top surface of the interlayer contacting the bottom surface of the buffer layer; and a waveguide layer comprising a top surface and a bottom surface, the top surface of the waveguide layer contacting the bottom surface of the interlayer.

14. The arrangement according to claim 13, wherein the fluorescence channel openings are formed as pyramids or cones or in upright form in the laminar substrate and extend at least as far as the buffer layer.

15. The arrangement according to claim 13, further comprising a plurality of lenses arranged on the top surface of the laminar substrate, each lens arranged in conjunction with a fluorescence channel opening.

16. The arrangement according to claim 13, further comprising a lens contacting the top surface of the laminar substrate.

17. The arrangement according to claim 13, further comprising a plurality of detectors arranged on the top surface of the laminar substrate, each detector arranged in conjunction with a fluorescence channel opening.

18. The arrangement according to claim 13, wherein the laminar substrate consists of a material that absorbs fluorescent light or is designed so as to reflect or absorb fluorescent light.

19. The arrangement according to claim 13, wherein the fluorescence channel openings are defined by at least one wall that reflects fluorescent light.

20. The arrangement according to claim 13, wherein the laminar substrate consists of silicon, glass, vitreous material, or a polymer and the buffer layer and waveguide layer consist of a silicate, glass, vitreous material, or a polymer.

21. The arrangement according to claim 13, further comprising a plurality of sample immobilization areas arranged on the top surface of the interlayer, each sample immobilization area arranged in conjunction with a fluorescence channel opening.

22. The arrangement according to claim 21, further comprising a plurality of immobilization layers contacting a plurality of the sample immobilization areas.

* * * * *